United States Patent
Chen

(10) Patent No.: US 7,582,456 B2
(45) Date of Patent: Sep. 1, 2009

(54) METHOD FOR SEPARATING, EXTRACTING AND PURIFYING POLY-β-HYDROXYALKANOATES (PHAS) DIRECTLY FROM BACTERIAL FERMENTATION BROTH

(75) Inventor: Xuejun Chen, Ningbo (CN)

(73) Assignee: Tianan Biologic Material Co., Ltd. Ningbo, Ninbgo (CN)

( * ) Notice: Subject to any disclaimer, the term of this patent is extended or adjusted under 35 U.S.C. 154(b) by 290 days.

(21) Appl. No.: 10/583,587

(22) PCT Filed: Dec. 19, 2003

(86) PCT No.: PCT/CN03/01092

§ 371 (c)(1),
(2), (4) Date: Jun. 19, 2006

(87) PCT Pub. No.: WO2005/059153

PCT Pub. Date: Jun. 30, 2005

(65) Prior Publication Data

US 2007/0072276 A1    Mar. 29, 2007

(51) Int. Cl.
*C12P 7/62*    (2006.01)
(52) U.S. Cl. ............................................. 435/135
(58) Field of Classification Search ................ None
See application file for complete search history.

(56) References Cited

U.S. PATENT DOCUMENTS

| 4,910,145 | A | | 3/1990 | Holmes et al. | |
|---|---|---|---|---|---|
| 5,110,980 | A | * | 5/1992 | Ramsay et al. | 560/185 |
| 5,391,708 | A | | 2/1995 | Hubbs et al. | |
| 5,451,456 | A | * | 9/1995 | Marchessault et al. | 428/327 |
| 5,536,419 | A | * | 7/1996 | Escalona et al. | 210/767 |
| 5,977,250 | A | * | 11/1999 | George et al. | 524/845 |

FOREIGN PATENT DOCUMENTS

| CN | 1190674 | A | | 8/1998 |
|---|---|---|---|---|
| CN | 1328160 | | * | 12/2001 |
| CN | 1328160 | A | | 12/2001 |

* cited by examiner

Primary Examiner—Herbert J. Lilling
(74) Attorney, Agent, or Firm—Butzel Long

(57) ABSTRACT

The invention discloses a method for directly separating and purifying polyhydroxyalkanoates in cells from fermentation liquid and it relates to the field of posttreatment technology of biological engineering. The method includes following steps: pretreating fermentation liquid with physical method for breaking cell wall; adjusting pH value of pretreated fermentation liquid to alkaline; adding anionic surfactant; reacting under agitation; separating and extracting coagulated precipitate from reaction liquid; washing and drying. The invention has the advantage of simple technology, low cost, high extraction yield and no pollution, and large scale industrialized production can be realized.

16 Claims, No Drawings

METHOD FOR SEPARATING, EXTRACTING AND PURIFYING POLY-β-HYDROXYALKANOATES (PHAS) DIRECTLY FROM BACTERIAL FERMENTATION BROTH

TECHNICAL FIELD

This invention relates to post treatment of biological engineering, particularly to extraction and separation of bacterial fermentation products, or more particularly to extraction and separation of polyhydroxyalkanoates in cells.

BACKGROUND OF THE INVENTION

Poly-β-hydroxyalkanoates (PHAs) are biological polyesters accumulated in cells by special microorganisms under special growth conditions.

The general formula of poly-β-hydroxyalkanoates is:

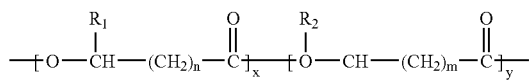

In which, n and m are integers from 1 to 4, and typically 1, that is for example 3-hydroxyalkanoates (3-HAS); $R_1$ and $R_2$ are straight chain or branched chain $C_{1-12}$ alkyl groups which are substituted or non-substituted; X and Y are not 0 simultaneously, and determine the content of the component in copolymer. The average molecular weight of PHAs is generally 1-4 million Da.

The physical property of PHAs is similar to that of polypropylene. As its biodegradability, biocompatibility, piezoelectric properties and optical activity are characteristics not possessed by common petrochemical resins, it has wide application prospects in industry, agriculture, medicine, sanitation, food, electronics, etc.

Large scale industrialized production of PHAs has not been realized internationally. The principal reason is because the cost is much higher than that of petrochemical resin. The cost of PHAs includes mainly material cost and separation purification cost. The material cost depends on production efficiency of bacteria species and fermentation technology, whilst the separation purification cost depends largely on technology. The current extraction technology includes separation of cells from fermentation liquid with high speed centrifuge and purification of PHAs in separated wet bacterial body with organic solvent extraction, chemical reagent or surfactant+enzyme. These methods suffer from high cost or serious pollution, and are difficult to be industrialized. A one step extraction separation method for extracting polyhydroxyalkanoates directly from fermentation liquid containing cells is disclosed in Chinese patent application CN1328160A, but it must use large quantities of sodium hypochlorite and has the defect of poor operation environment, serious pollution, cost increased by waste water treatment, and product quality affected by shear degradation of PHAs.

Chinese patent No. CN119067A discloses a method for separating and purifying polyhydroxyalkanoates in bacterial cells from bacterial thallus. The method includes two steps in extraction, which requires separation of bacterial thallus from fermentation liquid. As the bacterial thallus is very small (several microns) and the fermentation liquid has certain viscosity, it is necessary to use high speed centrifuge of separation factor higher than 6000. This greatly increases the investment and is a bottleneck in large scale industrialized production. The method also requires expensive protease to treat the separated product which increases cost.

The extraction method disclosed in Chinese patent CN1171410A requires high speed centrifuge and lyophilization of product separated with centrifuge. These are very difficult in large scale industrialized production. Taking a factory producing 100,000 tons of PHAS/year as example, nearly 3000-4000 tons of fermentation liquid/day will be centrifuged and 600-800 tons will be lyophilized. The industrial cost will be very high. The final washing with organic solvent pollutes the environment and increases product cost.

U.S. Pat. No 4,910,145 discloses a method for separating and extracting PHAS with enzyme and surfactant. Since the cell wall and membrane are very complicated in composition and cannot be completely decomposed with one enzyme, it is necessary to use several enzymes or a compound enzyme. As the optimal action conditions as pH, temperature, etc. of different enzymes are different, the technology is very complicated. The method requires heating fermentation liquid to >80° C. which consumes enormous energy. The price of enzyme preparation is high, so the separation cost is high. Besides, the purity of product is not high.

The purpose of this invention is to provide an extraction method for PHAs, which can effectively reduce separation and purification cost, reduces pollution, and is suitable for industrialized production.

Invention

This invention provides a method for directly separating and purifying polyhydroxyalkanoates in cells from bacterial fermentation liquid, which comprises:
(1) pretreating fermentation liquid with a physical method for breaking cell wall;
(2) adjusting the pH of the pretreated fermentation liquid so that it is alkaline;
(3) adding anionic surfactant and agitating;
(4) separating and extracting coagulated precipitate in reaction liquid;
(5) washing and drying.

The physical method includes mechanical breaking and ultrasonic breaking. The sequence of adjusting pH and adding surfactant is interchangeable. The mechanical breaking includes ball milling or high pressure homogenization.

In step 3, aside from adding anionic surfactant, coagulating agent can be added.

The mechanical breaking method used to break cell wall can be ball milling.

The pH of the pretreated fermentation liquid is adjusted to 8-13. The alkaline substance used in adjusting pH can be solid or an aqueous solution of NaOH, $Na_2CO_3$, $NaHCO_3$ or ammonia water.

The anionic surfactant can be olefinesulfonate (AOS), a fatty alcohol sulfate, a fatty alcohol polyoxyethylene-ether sulfate (AES), a fatty alcohol-polyoxyethylene ether (AEO), alkylphenol-polyoxyethylene ether, etc. The quantity of anionic surfactant is 0.5-20% (W/V) of fermentation liquid.

The coagulating agent is sodium polyacrylate, modified starch, polyamine, etc. The quantity of the coagulating agent is 0.5-20% (W/V) of the fermentation liquid.

After adding the anionic surfactant and the coagulating agent, the reaction temperature under agitation is 10-70° C. and the reaction time 5-60min.

Centrifuge, filter-press, vacuum suction filtration, etc. can be used for separating and extracting coagulated precipitate from the reaction liquid.

The invention is applicable to separation and purification of fermentation liquid of bacteria and its aberrance and gene engineering bacteria containing polyhydroxyalkanoates. Applicable bacteria include *Alcaligenes, Pseudomonas, Azotobacter, Rhodospirillum, Methylotrophs, Bacillus,* etc.

The invention has no high requirement for dry weight of cells and content of PHAs in fermentation liquid. The invention has the advantage of simple technology, low cost, high yield and greatly reduced pollution, so large scale industrialized production can be realized.

DETAILED DESCRIPTION OF THE INVENTION

The following examples are used to further describe the invention. These examples should not be construed as limiting the scope of claimed invention. Any modifications or changes made by the skilled man in the art benefited from the disclosure of this application should be included within the scope of claims stated in this application.

EXAMPLE 1

1000 ml of fermentation liquid of Alcaligenes entrophus mutant 65-7, in which the dry weight of cells was 142 g/l and the content of PHBV was 78.5% was pretreated with a ball mill (530 r/min, 0.1 mm steel ball) for 40 min. The pH of the resulting solution was adjusted to 12 with 30% NaOH solution. 13 g of sodium laurylsulfate was added to the solution and the temperature was adjusted to 32° C. while the solution was subjected to agitation for 5 min. The solution was filtered with suction and filter paper. The coagulated precipitate was washed with water until the washing liquid became neutral, then dried at 70° C. The purity of the product was 98.2%. The average molecular weight was $5.2 \times 10^5$ Da. The yield was 85.2%. The COD and BOD of waste water from suction filtration after treatment with anaerobic and aerobic bacteria is 800 and 30 mg/l respectively, in conformity with state discharge standards.

EXAMPLE 2

100 ml of fermentation liquid of *Alcaligenes entrophus,* in which the dry weight of cells was 147 g/l and the content of PHBV was 75.2% was subject to a process that broke the cell walls with ultrasonic (1500 W) for 20 min. The pH of the resulting solution was adjusted to 8 with 30% NaOH solution. 0.5 g of sodium laurylsulfate and 5 g of sodium polyacrylate were added to the solution and the temperature of the solution was adjusted to 70° C. while the solution was subjected to agitation for 30 min. The solution was filtered with suction and filter paper. The coagulated precipitate was washed with water until the washing liquid became neutral, then dried at 70° C. The purity of the product was 93.2%. The average molecular weight was $4.1 \times 10^5$ Da. The yield was 80.3%.

EXAMPLE 3

50 ml of fermentation liquid of *Alcaligenes entrophus,* in which the dry weight of cells was 102 g/l and the content of PHB was 60% was pretreated with a ball mill (560 r/min, 0.1 mm steel ball) for 30 min. The pH of the solution was adjusted to 13 with $NH_3.H_2O$ solution. 10 g of sodium laurylsulfate and 10 g of modified starch were added to the solution and the temperature of the solution was adjusted to 10° C. while the solution was subjected to agitation for 10 min. The solution was centrifuged (separation factor 600) and the coagulated precipitate was washed with water until the washing liquid became neutral, then dried at 70° C. The purity of the product was 98.2%. The average molecular weight was $4.4 \times 10^5$ Da. The yield was 87%.

EXAMPLE 4

500 ml of fermentation liquid of *Alcaligenes entrophus* mutant 65-7, in which the dry weight of cells was 135 g/l and the content of PHB was 75.5% was introduced into a vessel. The pressure in the vessel was increased to 60 MPa and rapidly released after 10 min and the liquid was collected. This operation was repeated twice. The pH of the solution was adjusted to 10 with 30% NaOH solution. 9 g of sodium lauryl polyoxyethylene ether sodium sulfate was added to the solution and the temperature of the solution was adjusted to 38° C. while the solution was subjected to agitation for 8 min. The solution was filtered with suction and filter paper. The coagulated precipitate was washed with water until the washing liquid became neutral. The purity of the product was 96.7%. The average molecular weight was $4.2 \times 10^5$. The yield was 81.5%.

EXAMPLE 5

100 ml of fermentation liquid of *Alcaligenes entrophus,* in which the dry weight of cells was 154 g/l and the content of PHBV was 80.5% was subject to a process that broke the cell walls with ultrasonic (2800 W, continuous treatment) for 40 min. The pH of the solution was adjusted to 11 with 30% NaOH solution 10 kg of sodium lauryl sulfate and 0.5 kg of sodium polyacrylate was added to the solution and the temperature to 50° C. while the solution was subjected to agitation for 60 min. The solution was filtered with a filter press. The coagulated precipitate was washed with water until the washing became neutral and the filtrate was dried in oven at 70° to a constant weight. The purity of the product was 97%. The average molecular weight was $5.3 \times 10^5$ Da. The yield was 84%.

EXAMPLE 6

100 ml of fermentation liquid of *Pseudomonas,* in which dry weight of cells was 86 g/l and the content of PHBV was 61.5% was pretreated with a ball mill (560 r/min, 0.1 mm steel ball) for 50 min. The pH of the solution was adjusted to 11 with 30% NaOH solution. 3 g of sodium laurylsulfate was added to the solution and the temperature of the solution was adjusted to 24° C. while the solution was subjected to agitation for 10 min. The solution was filtered with suction and filter paper. The coagulated precipitate was washed with water until the washing became neutral. The filtrate was dried at 70° C. to a constant weight. The purity of the product was 94.2%. The average molecular weight was $3.2 \times 10^5$ Da. The yield was 71.2%.

What is claimed is:

1. A method for directly separating and purifying polyhydroxyalkanoates in cells from a bacterial fermentation liquid, which comprises the steps of:
    a) physically pretreating a fermentation liquid containing cells to cause the walls of the cells to break;
    b) adjusting the pH value of the pretreated fermentation liquid from step a) to an alkaline condition;
    c) adding anionic surfactant to the solution of step b) and subjecting the solution to agitation;
    d) separating and extracting coagulated precipitate from the solution in step c); and
    e) washing and drying the coagulated precipitate, wherein the physical pretreatment includes mechanically breaking the cell walls or ultrasonically breaking the cell walls, and wherein steps b) and c) are interchangeable; wherein a coagulating agent is added in the step c) and wherein the coagulating agent comprises at least one of sodium polyacrylate, modified starch or polyamine.

2. The method according to claim 1, wherein the physical pretreatment comprises mechanically breaking the cell walls using ball milling.

3. The method according to claim 1, wherein the pH is adjusted in step b) to 8-13.

4. The method according to claim 1, wherein the pH is adjusted in step b) by adding at least one of NaOH, $Na_2CO_3$, $NaHCO_3$ or ammonia to the pretreated fermentation liquid.

5. The method according to claim 1, wherein the anionic surfactant added in step c) is at least one of olefin sulfonate, fatty alcohol sulfate, fatty alcohol polyoxyethylene ether sulfate, fatty alcohol polyoxyethylene ether or alkylphenol polyoxyethylene ether.

6. The method according to claim 1, wherein in step c) the temperature of the solution is adjusted to 10-70°C.

7. The method according to claim 1, wherein in step d) the coagulated precipitate is separated and extracted by means of a centrifuge, filter press or vacuum suction filtration.

8. The method according to claim 1, wherein the physical pretreatment comprises high pressure homogenization.

9. The method according to claim 3, wherein the pH is adjusted in step b) by adding at least one of NaOH, $Na_2CO_3$, $NaHCO_3$ or ammonia to the pretreated fermentation liquid.

10. The method according to claim 5, wherein the amount of anionic surfactant added in step c) is 0.5-20% (W/V) of the fermentation liquid.

11. The method according to claim 1, wherein the amount of coagulating agent added is 0.5-20% (W/V) of the fermentation liquid.

12. The method according to claim 1, wherein in step c) the solution is subjected to agitation for 5-60 min.

13. The method according to claim 6, wherein in step c) the solution is subjected to agitation for 5-60 min.

14. The method according to claim 4, wherein the NaOH, $Na_2CO_3$, $NaHCO_3$ is added as a solid.

15. The method according to claim 4, wherein the NaOH, $Na_2CO_3$, $NaHCO_3$ is added as a solution.

16. The method according to claim 4, wherein the ammonia comprises ammonia water.

* * * * *